US012736474B2

(12) United States Patent
Kim et al.

(10) Patent No.: US 12,736,474 B2
(45) Date of Patent: Sep. 15, 2026

(54) SYSTEM AND METHOD FOR CALCULATING SEA WATER TURBIDITY BASED ON SATELLITE IMAGE

(71) Applicant: Korea Institute of Ocean Science & Technology, Busan (KR)

(72) Inventors: Tae Sung Kim, Daejeon (KR); Jae Jin Park, Seoul (KR); Moonjin Lee, Daejeon (KR); Yong Myung Kim, Daejeon (KR)

(73) Assignee: Korea Institute of Ocean Science & Technology, Busan (KR)

( * ) Notice: Subject to any disclaimer, the term of this patent is extended or adjusted under 35 U.S.C. 154(b) by 99 days.

(21) Appl. No.: 18/930,137

(22) Filed: Oct. 29, 2024

(65) Prior Publication Data

US 2025/0180478 A1 Jun. 5, 2025

(30) Foreign Application Priority Data

Nov. 30, 2023 (KR) ........................ 10-2023-0171491

(51) Int. Cl.

*G01N 21/53* (2006.01)
*G01N 33/18* (2006.01)
*G06T 5/80* (2024.01)

(52) U.S. Cl.

CPC ........... *G01N 21/532* (2013.01); *G01N 33/18* (2013.01); *G06T 5/80* (2024.01); *G06T 2207/10032* (2013.01)

(58) Field of Classification Search

CPC ...... G01N 21/532; G01N 33/18; G01N 21/55; G01N 2021/1793; G01N 2201/0214; G06T 5/80; G06T 2207/10032

See application file for complete search history.

(56) References Cited

U.S. PATENT DOCUMENTS

2021/0247297 A1* 8/2021 Groeneveld ......... G06V 20/188
2021/0272321 A1* 9/2021 Jolliff ................... B64G 1/1021
2023/0154081 A1* 5/2023 Zhang ....................... G06T 5/77 382/162

FOREIGN PATENT DOCUMENTS

| | | | | |
|---|---|---|---|---|
| JP | 2017-138928 A | | 8/2017 | |
| KR | 10-2011-0067964 A | | 6/2011 | |
| KR | 10-2014-0062756 A | | 5/2014 | |
| KR | 20140062756 A | * | 5/2014 | ............... G06T 5/80 |
| KR | 10-1774871 B1 | | 8/2017 | |
| KR | 10-2019-0085745 A | | 7/2019 | |
| KR | 10-2366058 B1 | | 2/2022 | |
| KR | 10-2469002 B1 | | 11/2022 | |

OTHER PUBLICATIONS

English Translation of KWRC KR-20140062756-A Description (Year: 2014).*

* cited by examiner

*Primary Examiner* — Tarifur R Chowdhury
*Assistant Examiner* — Akbar H. Rizvi
(74) *Attorney, Agent, or Firm* — Dinsmore & Shohl LLP

(57) ABSTRACT

The present disclosure relates to a system and a method for calculating sea water turbidity based on a satellite image, which are configured to: collect sea water image data taken from a satellite, acquire remote sensing reflectance data by receiving and preprocessing the collected sea water image data, and calculate sea water turbidity based on the remote sensing reflectance data.

5 Claims, 2 Drawing Sheets

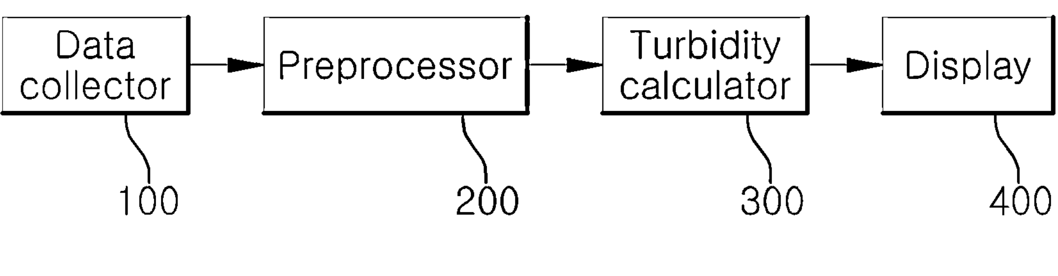
[FIG. 1]

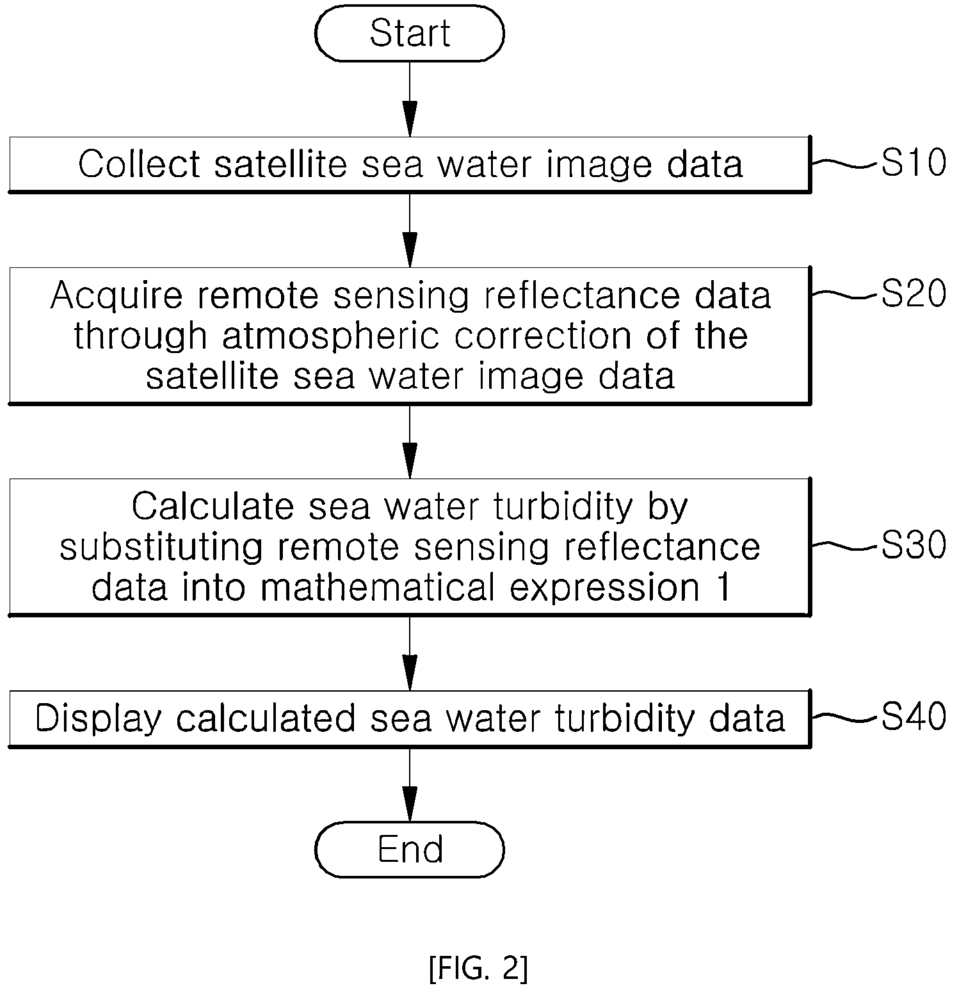
[FIG. 2]

SYSTEM AND METHOD FOR CALCULATING SEA WATER TURBIDITY BASED ON SATELLITE IMAGE

CROSS-REFERENCE TO RELATED APPLICATION

This application claims priority under 35 U.S.C § 119 to Korean Patent Application No. 10-2023-0171491 filed on Nov. 30, 2023, in the Korean Intellectual Property Office, the entire contents of which are hereby incorporated by reference.

BACKGROUND

Technical Field

The present disclosure relates to a system and a method for calculating sea water turbidity based on a satellite image, and more particularly, to a system and a method for calculating sea water turbidity based on a satellite image, which acquire remote sensing reflectance data by receiving and performing atmospheric correction of a satellite image, and calculate sea water turbidity by inputting the remote sensing reflectance data into a turbidity calculation formula.

Description of Related Technology

In recent researches, possibility of developing quantified algorithms using a remote sensing reflectance ratio on the coast having high turbidity has been suggested, and in this case, it can be known that the relationship between the reflectance ratio and the concentration of suspended solids is relatively insensitive to the characteristics of suspended particles. The turbidity is a physical quantity that can be used instead of the concentration of the suspended solids, and means water transparency which quantitatively represents the degree of water turbidity caused by underwater suspended solids or creatures. An automatic water quality measuring device is a device that measures water quality for a long period of time at short intervals on the coast or estuary, and measures the turbidity of the suspended solids instead of the concentration thereof.

An existing analysis algorithm has been developed based on actual measurement data collected in the clear ocean, and the corresponding algorithm has been collectively applied not only in the ocean but also on the coast. However, on the coast including complicated marine environments, the corresponding algorithm has limitations that indicate low accuracy in comparison to the ocean. Accordingly, in order to solve the above problems, there has been a need to develop a new algorithm in consideration of the optical characteristics and sea water components for coastal zones having high turbidity.

PRIOR ART DOCUMENTS

Patent Documents (Patent Document 1) Korean Registered Patent No. 10-2318169 (Title of invention: Sensor for measuring turbidity and suspended solids using transmitted and scattered light)

SUMMARY

The present disclosure has been devised to solve the above-described problems, and an object of the present disclosure is to provide a system and a method for calculating sea water turbidity based on a satellite image, which can calculate the sea water turbidity promptly and accurately.

In order to achieve the above object, a system for calculating sea water turbidity based on a satellite image according to an embodiment of the present disclosure includes: a data collector configured to collect sea water image data taken from a satellite; a preprocessor configured to acquire remote sensing reflectance data by receiving and preprocessing the collected sea water image data; and a turbidity calculator configured to calculate sea water turbidity based on the remote sensing reflectance data.

The system for calculating sea water turbidity based on a satellite image according to an embodiment may further include a display configured to display data of the sea water turbidity calculated by the turbidity calculator.

In the system for calculating sea water turbidity based on a satellite image according to an embodiment, the preprocessor may be configured to convert the reflectance data at an atmospheric top into ground reflectance data by receiving and performing atmospheric correction of the sea water image data, and the ground reflectance data may be the remote sensing reflectance data.

In the system for calculating sea water turbidity based on a satellite image according to an embodiment, the turbidity calculator may be configured to receive the remote sensing reflectance data and to calculate the sea water turbidity by a following mathematical expression 1.

$$(NTU) = 10^{1.715702 Rrs(560) + 0.969363} \quad \text{[Mathematical expression 1]}$$

(Where, NTU represents sea water turbidity, and Rrs(560) represents remote sensing reflectance of a green band (560 nm).)

In order to achieve the above object, a method for calculating sea water turbidity by using a system for calculating sea water turbidity based on a satellite image according to an embodiment of the present disclosure includes: collecting, by a data collector, sea water image data taken from a satellite; acquiring, by a preprocessor, remote sensing reflectance data by receiving and preprocessing the collected sea water image data; calculating, by a turbidity calculator, sea water turbidity based on the remote sensing reflectance data; and displaying, through a display, data of the sea water turbidity calculated in the step of calculating the turbidity.

The system and the method for calculating sea water turbidity based on a satellite image according to an embodiment of the present disclosure are configured to: collect sea water image data taken from a satellite, acquire remote sensing reflectance data by receiving and preprocessing the collected sea water image data, and calculate sea water turbidity based on the remote sensing reflectance data, and thus have an excellent effect of being able to calculate the sea water turbidity promptly and accurately.

BRIEF DESCRIPTION OF THE DRAWINGS

FIG. 1 is a block diagram of a system for calculating sea water turbidity based on a satellite image according to an embodiment of the present disclosure.

FIG. 2 is a flowchart explaining a method for calculating sea water turbidity based on a satellite image according to an embodiment of the present disclosure.

DETAILED DESCRIPTION

In describing embodiments of the present disclosure, when it is determined that the detailed description of the known technology which is related to the present disclosure may obscure the gist of the present disclosure, the detailed description will be omitted. In addition, technical terms, as will be mentioned hereinafter, are terms defined in consideration of their functions in the present disclosure, which may vary according to the intentions of users or operators, practices, or the like. Accordingly, the definition of the terms will be given based on the contents throughout the specification. The terminology used in the detailed description is merely for the purpose of describing the embodiments of the present disclosure, and thus should not be interpreted limitedly. As used herein, the singular forms are intended to include the plural forms unless being clearly used otherwise. In the description, the expressions "include", "have", and the like are to indicate the presence of features, integers, steps, operations, elements, some or combinations thereof, and thus should not be interpreted to preclude the presence or addition of one or more other features, integers, steps, operations, elements, some or combinations thereof.

It may be suggested that in association with each system illustrated in the drawings, elements with the same or different reference numerals may be different from or similar to each other in some cases. However, elements having different implementations may operate with some or all of the systems seen or described in the specification. Various elements illustrated in the drawings may be identical to or different from each other, and the use of the terms "first, second, and the like" to describe various elements is arbitrary.

In the specification, "transmission", "delivery", or "provision" of data or signals from any one constituent element to another constituent element means that any one constituent element transmits data or signals to another constituent element directly and through at least one other constituent element.

Hereinafter, embodiments of the present disclosure will be described in detail with reference to the drawings.

FIG. 1 is a block diagram of a system for calculating sea water turbidity based on a satellite image according to an embodiment of the present disclosure.

As illustrated in FIG. 1, a system for calculating sea water turbidity based on a satellite image according to an embodiment of the present disclosure may include a data collector 100, a preprocessor 200, a turbidity calculator 300, and a display 400, and may be constituted as one terminal device (e.g., notebook computer, personal computer, PDA, PMP, or smartphone) or a separate device.

The data collector 100 plays a role of collecting sea water image data taken from a satellite.

The preprocessor 200 plays a role of converting reflectance data at an atmospheric top into ground reflectance data (remote sensing reflectance data) by receiving and preprocessing (e.g., performing atmospheric correction of) the sea water image data collected by the data collector 100.

The atmospheric correction is a core process of removing the quantitative effect of the atmosphere from a signal received by a satellite sensor.

Level-2A image is created after passing through the atmospheric correction of Level-1C image, and a processor used in this case is Sen2Cor algorithm that is a SNAP software package.

Sen2Cor is a physically based approach, and is composed of calculations of geometries and altitudes of sensors and the sun and a radiation transfer function for atmospheric parameters.

Level-2A image includes surface reflectance in Band-1, 2, 3, 4, 5, 6, 7, 8, 8a, 9, 10, 11, and 12, to which the atmospheric correction has been applied.

The turbidity calculator 300 plays a role of receiving the remote sensing reflectance data from the preprocessor 200, and calculating the sea water turbidity by a following mathematical expression 1.

$$(NTU) = 10^{1.715702Rrs(560)+0.969363} \quad \text{[Mathematical expression 1]}$$

(Where, NTU represents sea water turbidity, and Rrs(560) represents remote sensing reflectance of a green band (560 nm).)

The display 400 plays a role of displaying data of the sea water turbidity calculated by the turbidity calculator 300. As the display 400, an output device, such as PDP, LCD, LED, or OLED, may be used.

A method for calculating sea water turbidity by using the above-described system for calculating sea water turbidity based on a satellite image according to an embodiment of the present disclosure will be described.

FIG. 2 is a flowchart explaining a method for calculating sea water turbidity based on a satellite image according to an embodiment of the present disclosure. Here, S means a step.

First, the data collector 100 collects sea water image data taken from a satellite (S10).

Next, the preprocessor 200 receives the sea water image data collected in the step S10, and acquires remote sensing reflectance data by preprocessing (performing atmospheric correction of) the sea water image data (S20).

Next, based on the acquired remote sensing reflectance data, the turbidity calculator 300 calculates sea water turbidity by a following mathematical expression 1.

$$(NTU) = 10^{1.715702Rrs(560)+0.96363} \quad \text{[Mathematical expression 1]}$$

(Where, NTU represents sea water turbidity, and Rrs(560) represents remote sensing reflectance of a green band (560 nm).)

Next, data of the sea water turbidity calculated in the step S30 is displayed through the display 400.

Meanwhile, although it is exemplified, in the above-described embodiment, that the sea water turbidity is calculated by inputting the remote sensing reflectance of a green band (560 nm) into the mathematical expression 1, the sea water turbidity may also be calculated by inputting the remote sensing reflectance data that is outputted from the preprocessor 200 into a machine learning model which is learned by the remote sensing reflectance data of the green band and the sea water turbidity data.

Since the system and the method for calculating sea water turbidity based on a satellite image according to an embodiment of the present disclosure are configured to: collect sea water image data taken from a satellite, acquire remote sensing reflectance data by receiving and preprocessing the collected sea water image data, and calculate sea water turbidity based on the remote sensing reflectance data, it is possible to calculate the sea water turbidity promptly and accurately.

In the drawings and the specification, although the optimum embodiment is disclosed and the specific terms are used, they are used merely for the purpose of explaining the embodiment of the present disclosure, but are not used to limit their meanings or the scope of the present disclosure defined in the claims. Accordingly, it will be able to be understood by those of ordinary skill in the art to which the present disclosure pertains that various modifications and other equivalent embodiments can be derived therefrom. Accordingly, the true technical scope of protection of the present disclosure should be determined by the technical idea of the appended claims.

DESCRIPTION OF SYMBOLS

100: data collector
200: preprocessor
300: turbidity calculator
400: display

What is claimed is:

1. A system for calculating sea water turbidity based on a satellite image, the system comprising:

a data collector (100) configured to collect sea water image data taken from a satellite;

a preprocessor (200) configured to acquire remote sensing reflectance data by receiving and preprocessing the collected sea water image data; and a turbidity calculator (300) configured to calculate sea water turbidity based on the remote sensing reflectance data, wherein the turbidity calculator (300) is configured to receive the remote sensing reflectance data and to calculate the sea water turbidity by a following mathematical expression 1:

$$(NTU) = 10^{1.715702Rrs(560)+0.969363},$$ [Mathematical expression 1]

and wherein, NTU represents sea water turbidity, and Rrs (560) represents remote sensing reflectance of a green band (560 nm).

2. The system of claim 1, further comprising:

a display (400) configured to display data of the sea water turbidity calculated by the turbidity calculator (300).

3. The system of claim 1, wherein the preprocessor (200) is configured to convert the reflectance data at an atmospheric top into ground reflectance data by receiving and performing atmospheric correction of the sea water image data, and wherein the ground reflectance data is the remote sensing reflectance data.

4. A method for calculating sea water turbidity by using a system for calculating sea water turbidity based on a satellite image, the method comprising:

collecting, by a data collector (100), sea water image data taken from a satellite;

acquiring, by a preprocessor (200), remote sensing reflectance data by receiving and preprocessing the collected sea water image data;

calculating, by a turbidity calculator (300), sea water turbidity based on the remote sensing reflectance data; and displaying, through a display (400), data of the sea water turbidity calculated in the step of calculating the turbidity, wherein the turbidity calculator (300) is configured to receive the remote sensing reflectance data and to calculate the sea water turbidity by a following mathematical expression 1:

$$(NTU) = 10^{1.715702Rrs(560)+0.969363},$$ [Mathematical expression 1]

and wherein, NTU represents sea water turbidity, and Rrs (560) represents remote sensing reflectance of a green band (560 nm).

5. The method of claim 4, wherein the preprocessor (200) is configured to convert the reflectance data at an atmospheric top into ground reflectance data by receiving and performing atmospheric correction of the sea water image data, and wherein the ground reflectance data is the remote sensing reflectance data.

* * * * *